United States Patent
Sournac et al.

(10) Patent No.: US 8,114,139 B2
(45) Date of Patent: Feb. 14, 2012

(54) OSTEOSYNTHESIS PLATE

(75) Inventors: Denys Sournac, Reyrieux (FR);
Jean-Philippe Caffiero, Lyons (FR);
François Carlier, Guerande (FR)

(73) Assignee: Medicrea Technologies, La Rochelle (FR)

( * ) Notice: Subject to any disclaimer, the term of this patent is extended or adjusted under 35 U.S.C. 154(b) by 521 days.

(21) Appl. No.: 12/298,657

(22) PCT Filed: Apr. 20, 2007

(86) PCT No.: PCT/IB2007/001033
§ 371 (c)(1),
(2), (4) Date: Oct. 27, 2008

(87) PCT Pub. No.: WO2007/125395
PCT Pub. Date: Nov. 8, 2007

(65) Prior Publication Data
US 2009/0234393 A1      Sep. 17, 2009

(30) Foreign Application Priority Data
Apr. 27, 2006  (FR) ..................................... 06 03746

(51) Int. Cl.
*A61B 17/80* (2006.01)
(52) U.S. Cl. ........ 606/286; 606/289; 606/290; 606/291; 606/292; 606/293; 606/295; 606/296
(58) Field of Classification Search .................. 606/286, 606/289–296
See application file for complete search history.

(56) References Cited

U.S. PATENT DOCUMENTS

| | | | | |
|---|---|---|---|---|
| 5,549,612 A | * | 8/1996 | Yapp et al. | 606/293 |
| 5,578,034 A | * | 11/1996 | Estes | 606/281 |
| 5,876,402 A | * | 3/1999 | Errico et al. | 606/287 |
| 6,258,089 B1 | * | 7/2001 | Campbell et al. | 606/86 B |
| 6,602,255 B1 | * | 8/2003 | Campbell et al. | 606/290 |
| 6,626,907 B2 | * | 9/2003 | Campbell et al. | 606/86 B |
| 2003/0225409 A1 | * | 12/2003 | Freid et al. | 606/69 |
| 2004/0127896 A1 | * | 7/2004 | Lombardo et al. | 606/61 |
| 2005/0021032 A1 | * | 1/2005 | Koo | 606/69 |
| 2006/0195100 A1 | * | 8/2006 | Kirschman | 606/69 |

FOREIGN PATENT DOCUMENTS

| | | |
|---|---|---|
| DE | 4409833 | 10/1995 |
| EP | 0599640 | 6/1994 |
| EP | 1486175 | 12/2004 |
| FR | 2778088 | 11/1999 |
| WO | 0024325 | 5/2000 |

OTHER PUBLICATIONS

International search report in corresponding PCT/IB2007/001033.

* cited by examiner

*Primary Examiner* — Thomas C. Barrett
*Assistant Examiner* — Zade Coley
(74) *Attorney, Agent, or Firm* — Young & Thompson

(57) ABSTRACT

A plate (1) includes blocking elements (4b, 5, 6) including:
at least one slot (5) comprising a first portion opening into the hole (2) and a second portion extending over a section of this hole (2), at a distance from the edge defining this hole (2), this slot (5) thereby isolating a portion of material (6); this portion (6) has a first part (6a) with a radially increased thickness and a second part (6b) having a radially reduced thickness; this part (6b) has a thickness such that the portion (6) may be radially mobile between a withdrawn position and an active position;
a pad (4b) engaged in the slot (5), able to be moved in such a way as to bring the portion of material (6) from its withdrawn position to its active position.

13 Claims, 2 Drawing Sheets

OSTEOSYNTHESIS PLATE

BACKGROUND OF THE INVENTION

1. Field of the Invention

The present invention relates to an osteosynthesis plate, in particular for vertebral osteosynthesis, and in particular a plate intended for the osteosynthesis of cervical vertebrae.

2. Description of the Related Art

An osteosynthesis plate is generally fixed using screws engaged through holes formed in the plate. This type of fixing may, in some cases, involve a risk of the screws coming unscrewed, which leads to the possibility of movement of the bone parts that are supposed to be maintained by the plate. This is particularly the case for an osteosynthesis plate for cervical vertebrae, given that these vertebrae are subject to repeated stress and that the extent to which the screws are supported in these vertebrae is reduced due to the reduced dimensions of these screws.

A number of systems have been conceived making it possible to prevent the back-out of screws from osteosynthesis plates, for example back-plates screwed onto the plate, at least partially covering the screws after their insertion.

The existing systems, however, have the drawback of not simultaneously meeting the following needs:
simplicity of structure and relative ease of production;
reduced production cost;
ease and speed of implementation;
perfect anti-backout action of the screws;
possible reversibility of this anti-backout action, in the case where one or several screws must be removed.

SUMMARY OF THE INVENTION

The present invention aims to correct this fundamental drawback by providing a plate which simultaneously meets these various goals.

The plate in question comprises, in a known manner, receiving holes for screws or similar fixing bodies and blocking means of at least one screw as regards extraction with respect to the hole receiving this screw.

According to the invention, said blocking means comprise:
at least one slot comprising a first portion opening into the hole and a second portion extending over a section of this hole, at a distance from the edge defining this hole, this slot thereby isolating a portion of material; said second portion of the slot has, on one side of the first portion of the slot, a first area of a radially reduced thickness and, on the side opposite this first portion of the slot, a second area of a radially greater thickness, such that said portion of material itself has, on one side of said first portion of the slot, a first part with a radially increased thickness and, on the side opposite said first portion of the slot, a second part having a radially reduced thickness; this second part has a thickness such that the portion of material may be radially mobile between a withdrawn position, in which the portion of material does not extend above the surface of the hole, and an active position, in which the portion of material extends partially over this area;
a sliding nut engaged in said slot, said nut having a thickness smaller than that of the second area but greater than that of the first area, able to be moved from this second area toward the first area in such a way as to bring said portion of material from its withdrawn position to its active position.

The realization of blocking means thus only involves developing said portion of material, developing the sliding nut and engaging this sliding nut in said slot. The sliding nut makes it possible to keep said portion of material completely in the active position, providing blocking action of the screw. This sliding nut may, if necessary, be returned to said second area of the slot, enabling said portion of material to return to the withdrawn position, and therefore allowing the possibility of reversing the blocking action of the screw.

Advantageously, said portion of material and/or the sliding nut comprises a slanted wall making it possible to facilitate the passage of the sliding nut from said second area to said first area and therefore to facilitate bringing said portion of material to the active position.

Preferably, the plate comprises several slots and several sliding nuts, preferably distributed regularly on the circumference of the hole, in order to provide blocking of the screw at several points.

Complete blocking action is thus provided.

According to one preferred embodiment of the invention in this case, the sliding nuts of the different slots are connected to each other by a same piece intended to be placed along the length of the plate, in particular by a ring intended to be placed coaxially in relation to the hole.

Pivoting this piece makes it possible to achieve simultaneous movement of the various sliding nuts, and therefore to simultaneously bring the various portion of materials into the active position.

Simple actuation of the blocking means is thus obtained.

Preferably, each portion of material is made of a material having a degree of elastic return, and the first part of this portion of material has a large contact surface with the sliding nut and/or the sliding nut has a large contact surface with the edge of the plate defining the slot.

The combination of this elastic return and this or these large contact surface(s) makes it possible to maintain the sliding nut in this first part by simple friction.

Advantageously, each portion of material is made up of the same material as the plate, each slot being developed in the material making up the plate.

It is thus particularly simple to produce said portion of material by placing the slot in the material of the plate.

Preferably, each sliding nut comprises means enabling it to be latched through said second area of the slot, such that its insertion on the plate is simple. When multiple such sliding nuts are connected to a same piece, in particular when the plate comprises the aforementioned ring, this piece is easily and quickly mounted on the plate by engagement and latching of the various sliding nuts in the corresponding second areas of the various slots.

BRIEF DESCRIPTION OF THE DRAWING FIGURES

The invention will be better understood, and other characteristics and advantages of the invention will be explained, in reference to the annexed diagrammatic drawing, showing, as a non-exhaustive example, a preferred embodiment of the plate of the invention.

DETAILED DESCRIPTION OF THE INVENTION

Figure 1:
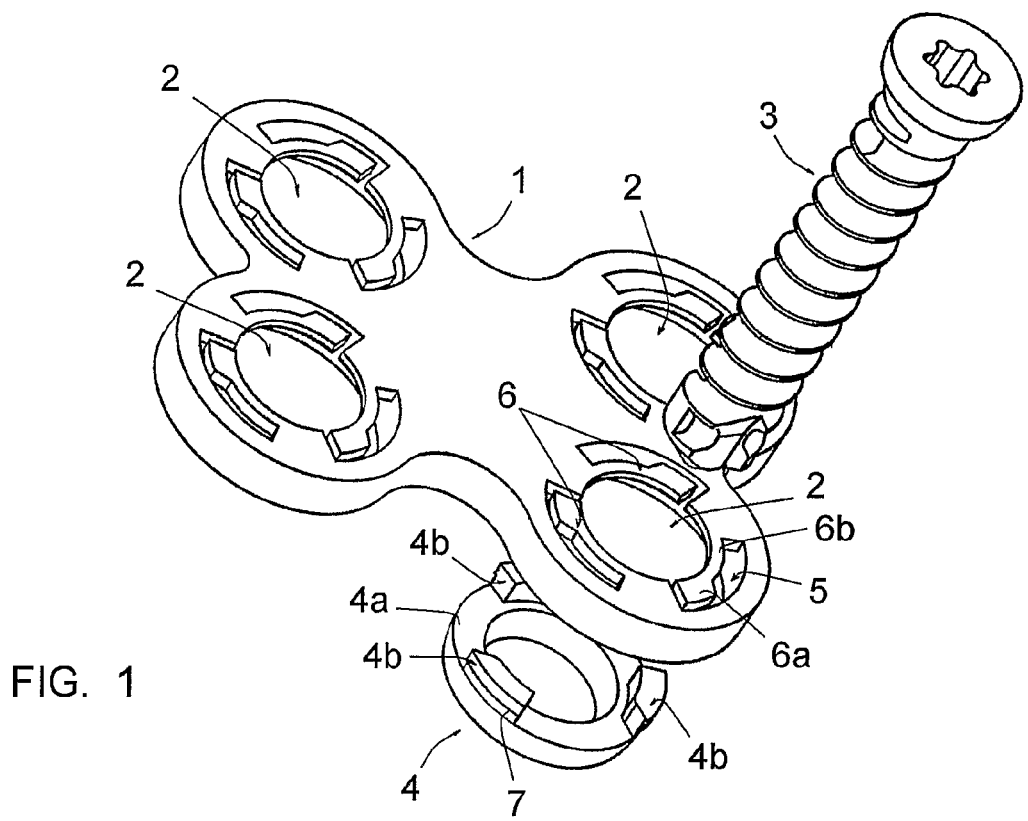
FIG. 1 is a perspective view with, in exploded view, a ring which may receive one of the holes it comprises and a screw intended to be engaged in this hole.

FIG. 1 shows an osteosynthesis plate 1, in particular for osteosynthesis of cervical vertebrae, comprising four holes 2 for its fixing to two consecutive cervical vertebrae using screws 3 engaged in these holes, only one screw 3 being illustrated. This plate 1 is made of a suitable metallic material, particularly stainless steel or titanium.

Figure 2:
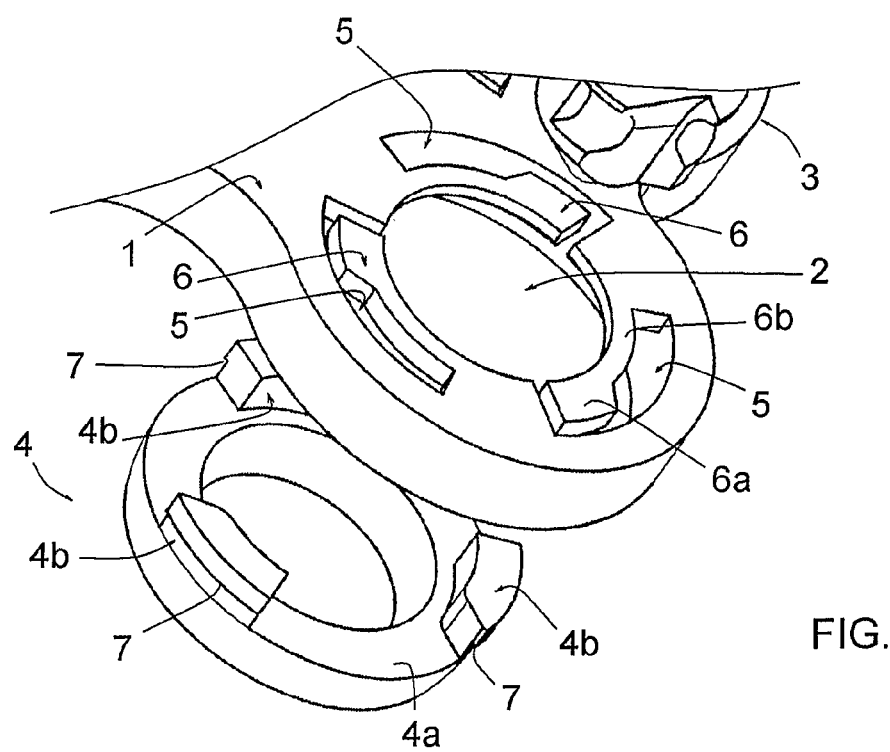
FIG. 2 is a partial view of the plate, the ring and the screw, enlarged.

As is shown more specifically in FIG. 2, the plate comprises four bores coaxial to the holes 2, reducing its thickness at the level of these holes 2 and forming housings to receive four rings 4, only one of which is illustrated in FIG. 1.

In its residual thickness, the plate 1 comprises, at the level of each hole 2, three slots 5 distributed regularly on the circumference of the hole 2.

Each slot 5 comprises a first portion, developed radially in relation to the hole 2 and opening into this hole, and a second portion, curved, extending on a sector of this hole 2 at a distance from the edge defining this hole, the slot 5 thereby isolating a portion of material 6.

Said second portion of the slot 6 has, on one side of the first portion of the slot, a first area having a radially reduced thickness and, on the side opposite this first portion of the slot, a second area having a more significant radial thickness, such that said portion of material 6 has, on one side of the first portion of the slot, a first part 6a having a radially increased thickness and, on the side opposite said first portion of the slot, a second part 6b having a more radially reduced thickness. This second part 6b has a thickness such that the portion of material 6 may be radially mobile between a withdrawn position, shown in FIG. 4, in which each portion of material 6 does not extend above the area of the hole 2, and an active position, shown in FIG. 5, in which the portion of material 6 partially extends above this area.

The portion of material 6 also comprises a slanted wall between said first part 6a and second part 6b, forming a ramp.

Each ring 4 has a round base part 4a and three pads 4b distributed regularly on its circumference.

The base part 4a is sized to fit in the aforementioned bore, snugly but with the possibility of pivoting the ring 4 in this bore.

Figure 3:
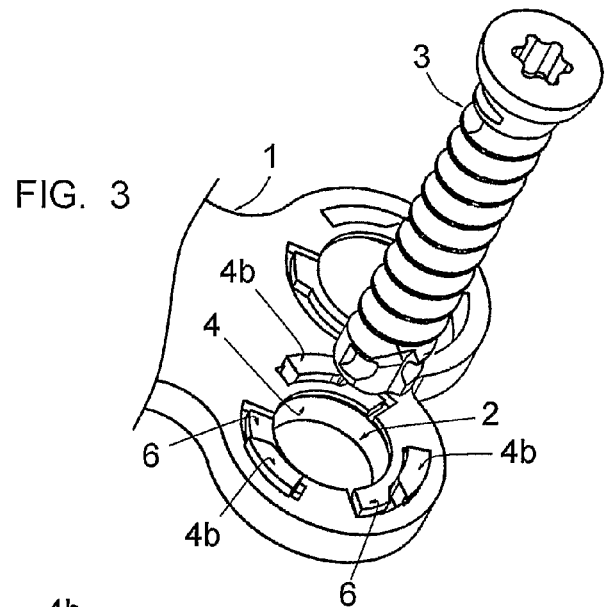
FIG. 3 is a partial view of the plate, the ring and the screw after mounting of the ring on the plate.

Each pad 4b has a thickness slightly less than that of said second areas of the slots 5, but greater than that of said first areas of these slots. The pads 4b are moreover disposed so that they may be simultaneously engaged in said second areas of the slots 5, as shown in FIG. 3, and can slide from said second portions of the slots 5 to said first portions of these slots and inversely, as one can see by comparing FIGS. 4 and 5.

Figure 5:
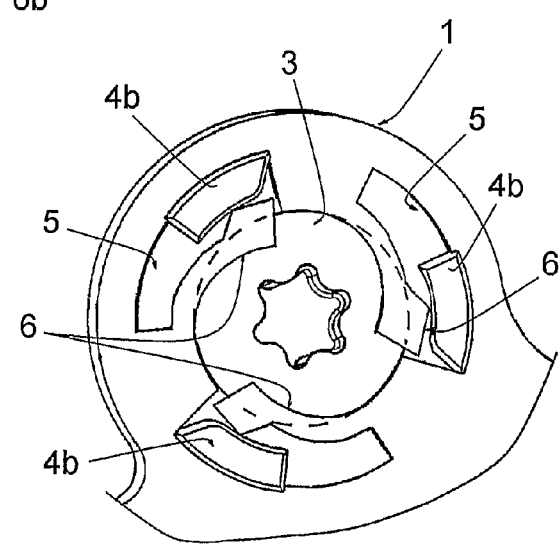
FIG. 5 is a view similar to FIG. 4, after axial blocking of the screw.

Each pad 4b has a significant length such that, when it is located in said first portion of the slot 5 in which it is engaged, it has large contact surfaces with the first part 6a of the portion of material 6 and with the plate 1, such that it can be maintained in the position shown in FIG. 5 by friction and elastic return of the portion of material 6.

Each pad 4b moreover comprises a step 7 on its radially outside surface, such that it has a slightly increased thickness in its upper part. As can be understood from the figures, these steps 7 enable an insertion of the ring 4 on the plate 1, made possible thanks to the slight flexibility of the second parts 6b of the portion of materials 6.

Furthermore, each pad 4b has a slanted lateral surface, turned, after assembly, toward said slanted wall separating said first part 6a and second part 6b. This slanted lateral surface cooperates with this slanted wall to facilitate the passage of each pad 4b from said second area of the slot 5 toward said first area of this slot 5.

In practice, the plate 1 is simply formed by engaging the rings 4 in the aforementioned bores and latching steps 7 onto it.

Figure 4:
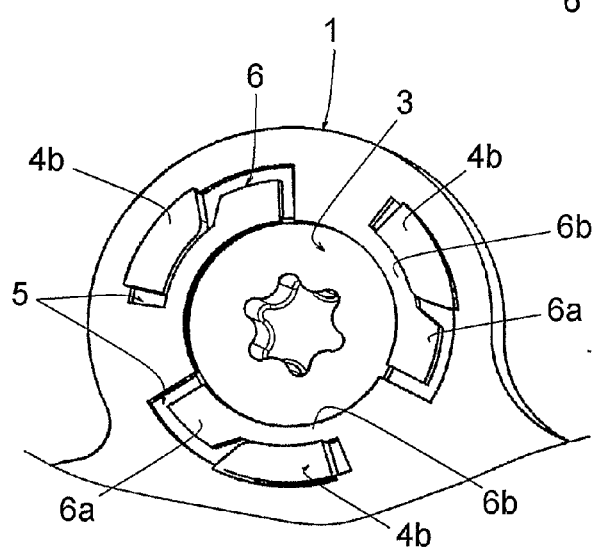
FIG. 4 is a partial view of the plate, the ring and the screw after insertion of the screw and before axial blocking of said screw.

During insertion of the plate 1 on vertebrae, each ring 4 finds itself in the angular position shown in FIG. 4, in which the pads 4b are in said second areas of the slots 5 and, consequently, the portion of materials 6 are in their inactive positions. The screws 3 can then be inserted through the holes 2. Once these screws 3 have been fully inserted, the rings 4 are pivoted clockwise in FIG. 4, using a suitable instrument being supported on the pads 4b, in such a way as to cause these pads 4b to move from the position shown in FIG. 4 to the position shown in FIG. 5. The pads 4b are then frictionally inserted between the radially outside edges of the slots 5 and said first parts 6a, between which they are fixed. The portion of materials 6 are then moved into their active positions shown in FIG. 5, in which they extend above the perimeter of the hole 2, therefore in front of the heads of the screws 3, and thereby provide effective axial blocking of these screws 3.

If it becomes necessary to remove a screw 3, the aforementioned instrument can be used to return the pads 4b to their positions shown in FIG. 4, thereby enabling removal of the screw 3.

As shown by the preceding, the invention provides an osteosynthesis plate, in particular for osteosynthesis of cervical vertebrae, having the primary advantage of simultaneously meeting the following objectives:

simplicity of structure and relative ease of production;
reduced production cost;
ease and speed of implementation;
perfect anti-backout action of the screws;
possible reversibility of this anti-backout action.

It goes without saying that the invention is not limited to the embodiment described above as an example, but that it extends to all embodiments covered by the annexed claims.

The invention claimed is:

1. An osteosynthesis plate (1), comprising:
   receiving holes (2) configured for screws (3) or similar fixing bodies; and
   means for blocking (4b, 5, 6) of at least one screw (3) as regards extraction with respect to the hole (2) receiving this screw (3), wherein said means for blocking comprise:
   a plurality of slots, each slot (5) comprising a first portion opening into the hole (2) and developed radially in relation to the hole (2) a second portion extending over a section of the hole (2), at a distance from an edge defining the hole (2), the slot (5) thereby isolating a portion of material (6); said second portion of the slot (5) has, on a side of the first portion of the slot (5), a first area of a radially reduced thickness and, on a side opposite the first portion of the slot (5), a second area of a radially greater thickness, such that said portion of material (6) itself has, on the side of said first portion of the slot (5), a first part (6a) with a radially increased thickness and, on the side opposite said first portion of the slot (5), a second part (6b) having a radially reduced thickness; the second part (6b) has a thickness such that the portion of material (6) may be radially mobile between a withdrawn position, in which the portion of material (6) does not extend above a surface of the hole (2), and an active position, in which the portion of material extends partially over the area so as to axially block a screw in the hole (2); and a plurality of pads, each pad (4b) engaged in said slot (5), said pad having a thickness smaller than that of the second area but greater than that of the first area, able to be slidingly moved along said second portion of said slot, from said second area toward said first area in such a way as to bring said portion of material (6) from its withdrawn position to its active position, wherein the pads (4b) of the different slots (5) are connected to each other by a ring configured to be placed coaxially in relation to the hole (2).

2. The osteosynthesis plate (1) according to claim 1, wherein said portion of material (6) and/or the pad (4b) comprises a slanted wall making it possible to facilitate the passage of the pad (4b) from said second area to said first area.

3. The osteosynthesis plate (1) according to claim 1, wherein the slots (5) and the pads (4b) are distributed regularly on a circumference of the hole (2).

4. The osteosynthesis plate (1) according to claim 1, wherein each portion of material (6) is made of a material having a degree of elastic return, and the first part (6a) of this portion of material (6) has a large contact surface with the pad (4b) and/or the pad (4b) has a large contact surface with the edge of the plate (1) defining the slot (5).

5. The osteosynthesis plate (1) according to claim 1, wherein each portion of material (6) is made up of the same material as the plate (1), each slot (5) being developed in the material making up the plate (1).

6. The osteosynthesis plate (1) according to claim 1, wherein each pad (4b) comprises means for latching through said second area of the slot (5).

7. The osteosynthesis plate (1) according to claim 2, wherein the slots (5) and the pads (4b) are distributed regularly on the circumference of the hole (2).

8. The osteosynthesis plate (1) according to claim 2, wherein each portion of material (6) is made of a material having a degree of elastic return, and the first part (6a) of this portion of material (6) has a large contact surface with the pad (4b) and/or the pad (4b) has a large contact surface with the edge of the plate (1) defining the slot (5).

9. The osteosynthesis plate (1) according to claim 3, wherein each portion of material (6) is made of a material having a degree of elastic return, and the first part (6a) of this portion of material (6) has a large contact surface with the pad (4b) and/or the pad (4b) has a large contact surface with the edge of the plate (1) defining the slot (5).

10. The osteosynthesis plate (1) according to claim 2, wherein each portion of material (6) is made up of the same material as the plate (1), each slot (5) being developed in the material making up the plate (1).

11. The osteosynthesis plate (1) according to claim 2, wherein each pad (4b) comprises means for latching through said second area of the slot (5).

12. An osteosynthesis plate (1), comprising:
receiving holes (2) configured for screws (3) or similar fixing bodies; and
a blocking apparatus (4b, 5, 6) of at least one screw (3) as regards extraction with respect to the hole (2) receiving this screw (3), said blocking apparatus comprising:
a plurality of slots, each slot (5) comprising a first portion opening into the hole (2) and developed radially in relation to the hole (2) a second portion extending over a section of the hole (2), at a distance from an edge defining the hole (2), the slot (5) thereby isolating a portion of material (6); said second portion of the slot (5) has, on a side of the first portion of the slot (5), a first area of a radially reduced thickness and, on a side opposite the first portion of the slot (5), a second area of a radially greater thickness, such that said portion of material (6) itself has, on the side of said first portion of the slot (5), a first part (6a) with a radially increased thickness and, on the side opposite said first portion of the slot (5), a second part (6b) having a radially reduced thickness; this second part (6b) has a thickness such that the portion of material (6) may be radially mobile between a withdrawn position, in which the portion of material (6) does not extend above a surface of the hole (2), and an active position, in which the portion of material extends partially over the area so as to axially block a screw in the hole (2);
a plurality of pads, each pad (4b) engaged in said slot (5), said pad having a thickness smaller than that of the second area but greater than that of the first area, able to be slidingly moved along said second portion of said slot, from said second area toward said first area in such a way as to bring said portion of material (6) from its withdrawn position to its active position wherein the pads (4b) of the different slots (5) are connected to each other by a ring configured to be placed coaxially in relation to the hole (2).

13. The osteosynthesis plate (1) according to claim 12, wherein said portion of material (6) and/or the pad (4b) comprises a slanted wall making it possible to facilitate the passage of the pad (4b) from said second area to said first area.

* * * * *